United States Patent
Herrin et al.

(10) Patent No.: US 11,151,517 B2
(45) Date of Patent: Oct. 19, 2021

(54) METHOD TO DETERMINE, REMIND AND VALIDATE MEDICATION USAGE

(71) Applicant: International Business Machines Corporation, Armonk, NY (US)

(72) Inventors: Bradley C. Herrin, Marina Del Ray, CA (US); Morris S. Johnson, Jr., Cary, NC (US); Jarett Stein, Bryn Mawr, PA (US); Xianjun Zhu, Durham, NC (US)

(73) Assignee: International Business Machines Corporation, Armonk, NY (US)

( * ) Notice: Subject to any disclaimer, the term of this patent is extended or adjusted under 35 U.S.C. 154(b) by 713 days.

(21) Appl. No.: 15/496,071

(22) Filed: Apr. 25, 2017

(65) Prior Publication Data

US 2018/0307799 A1 Oct. 25, 2018

(51) Int. Cl.
| | |
|---|---|
| *G06Q 10/10* | (2012.01) |
| *G16H 80/00* | (2018.01) |
| *G16H 20/13* | (2018.01) |
| *G16H 50/70* | (2018.01) |
| *G16H 40/67* | (2018.01) |
| *G16H 10/60* | (2018.01) |

(52) U.S. Cl.
CPC ........... *G06Q 10/109* (2013.01); *G16H 10/60* (2018.01); *G16H 20/13* (2018.01); *G16H 40/67* (2018.01); *G16H 50/70* (2018.01); *G16H 80/00* (2018.01)

(58) Field of Classification Search
CPC ...... G06Q 10/109; G16H 80/00; G16H 40/67; G16H 10/60; G16H 50/70; G16H 20/13
USPC .......................................................... 705/2
See application file for complete search history.

(56) References Cited

U.S. PATENT DOCUMENTS

| | | |
|---|---|---|
| 5,020,037 A | 5/1991 | Raven |
| 6,294,999 B1 | 9/2001 | Yarin et al. |

(Continued)

FOREIGN PATENT DOCUMENTS

WO     2007021496 A2     2/2007

OTHER PUBLICATIONS

Silva, V.J., et al., "UbMed: A Ubiquitous System for Monitoring Medication Adherence", 2016 IEEE 18th International Conference on e-Health Networking, Applications and Service (Healthcom), Sep. 14-16, 2016.

(Continued)

*Primary Examiner* — Robert A Sorey
*Assistant Examiner* — Kimberly A. Sass
(74) *Attorney, Agent, or Firm* — Scully, Scott, Murphy & Presser, P.C.; Scott Dobson, Esq.

(57) ABSTRACT

A method, system, and computer product for prompting a patient to take a medicine including collecting medicine prescription information associated with a patient, collecting medicine usage data associated with the patient, comparing the medicine usage data with the medicine prescription information, determining whether a medicine is taken by the patient as prescribed in the prescription information based on a comparison result of the medicine usage data and the prescription information, and generating one or more control signals to interrupt operations of one or more devices within an environment of the patient or environments of the patient's family member or caregivers, in response to determining that the medicine is not taken as prescribed.

20 Claims, 6 Drawing Sheets

(56) References Cited

U.S. PATENT DOCUMENTS

| | | | |
|---|---|---|---|
| 8,092,224 | B2 | 1/2012 | Walker et al. |
| 9,015,054 | B2 | 4/2015 | Lara et al. |
| 2007/0016443 | A1 | 1/2007 | Wachman et al. |
| 2007/0097792 | A1 | 5/2007 | Burrows et al. |
| 2010/0174229 | A1* | 7/2010 | Hsu .................. A61M 5/142 604/66 |
| 2013/0173305 | A1 | 7/2013 | Hyde et al. |
| 2014/0219064 | A1 | 8/2014 | Filipi et al. |
| 2016/0132660 | A1* | 5/2016 | Barajas ............. G06Q 10/10 705/2 |
| 2016/0217272 | A1 | 7/2016 | Panzini et al. |
| 2016/0267249 | A1 | 9/2016 | High et al. |
| 2017/0041454 | A1* | 2/2017 | Nicholls ............. H04L 67/16 |

OTHER PUBLICATIONS

Atayero, A.A., et al., "Development of Smart Assistive DTMF Home Automation System for Ageing Population", Proceedings of the World Congress on Engineering and Computer Science 2016, WCECS 2016, Oct. 19-21, 2016, 5 pages, vol. I.

Hayes, T.L., et al., "An Electronic Pillbox for Continuous Monitoring of Medication Adherence", Conf Proc IEEE Eng Med Biol Soc., Author manuscript, Jul. 28, 2010, pp. 1-9.

Ho, L., et al., "A Prototype on RFID and Sensor Networks for Elder Healthcare: Progress Report", SIGCOMM'05 Workshops, Aug. 22-26, 2005, pp. 70-75.

Proteus Digital Health, "U.S. FDA Accepts First Digital Medicine New Drug Application for Otsuka and Proteus Digital Health", http://www.proteus.com/press-releases/u-s-fda-accepts-first-digital-medicine-new-drug-application-for-otsuka-and-proteus-digital-health/, Sep. 10, 2015, Accessed on Apr. 21, 2017, 9 pages.

* cited by examiner

METHOD TO DETERMINE, REMIND AND VALIDATE MEDICATION USAGE

FIELD

The present disclosure relates to determining, reminding, and validating medicine usage of patients by comparing medicine usage data for a patient with medicine prescription information for that patient.

BACKGROUND

It is known that medicines (or medications) work best when taken as prescribed. Not only do patients get the best outcomes, but so do parents, caregivers, physicians, and healthcare companies. For instance, a prescription is written to take it for twice a day, but a patient may forget to take the medicines and only take the medicines once a day instead of twice as prescribed. Some patients use a pill daily-reminder box or inhalers with counters to help them remind usage of the medicines, but the patients still need to voluntarily take the medicines.

SUMMARY

In an aspect of the present disclosure, a computer-implemented method for prompting a patient to take a medicine is provided. The method includes collecting medicine prescription information associated with a patient, collecting medicine usage data associated with the patient, comparing the medicine usage data with the medicine prescription information, determining whether a medicine is taken by the patient as prescribed in the prescription information based on a comparison result of the medicine usage data and the prescription information, and generating one or more control signals to interrupt operations of one or more devices within an environment of the patient or environments of the patient's family member or caregivers, in response to determining that the medicine is not taken as prescribed.

In an aspect of the present disclosure, a system for prompting a patient to take a medicine is provided. The system includes one or more processors and a memory device coupled to the one or more processors. The memory stores processor-executable program instructions. The one or more processors, when executing the program instructions, are configured to collect medicine prescription information associated with a patient, collect medicine usage data associated with the patient, compare the medicine usage data with the medicine prescription information, determine whether a medicine is taken by the patient as prescribed in the prescription information based on a comparison result of the medicine usage data and the prescription information, and generate one or more control signals to interrupt operations of one or more devices within an environment of the patient or environments of the patient's family member or caregivers, in response to determining that the medicine is not taken as prescribed.

In an aspect of the present disclosure, a computer program product comprising a computer readable storage medium having computer readable program instructions embodied therewith is provided. The computer readable program instructions executable by at least one processor to cause a computer to perform a method for prompting a patient to take a medicine. The method includes collecting medicine prescription information associated with a patient, collecting medicine usage data associated with the patient, comparing the medicine usage data with the medicine prescription information, determining whether a medicine is taken by the patient as prescribed in the prescription information based on a comparison result of the medicine usage data and the prescription information, and generating one or more control signals to interrupt operations of one or more devices within an environment of the patient or environments of the patient's family member or caregivers, in response to determining that the medicine is not taken as prescribed.

DETAILED DESCRIPTION

Embodiments of the present disclosure will now be described in detail with reference to the drawings. However, the following embodiments do not restrict the invention claimed in the claims. Moreover, all combinations of features described in the embodiments are not necessarily mandatory for the architecture of the present invention. Like numbers are assigned to like elements throughout the description of the embodiments of the present invention.

According to exemplary embodiments of the present disclosure, a method, system, and computer product for tracking a "medical adherence", ensuring that the medicine is being taken by a patient as prescribed, and prompting the patient to take the medicine, so that the medicine can work best. If a patient is not taking his/her medicine as prescribed, the system (e.g., 10 of FIG. 1) according to an embodiment may interface one or more end-user devices within a specific environment of the patient or external environments of remotely located family members or caregivers of the patient to interrupt operations of the end-user devices and prompt the patient to take the medicines. The term "medical adherence" may be understood to mean a degree to which a patient correctly follows instructions in a prescription.

Figure 1:
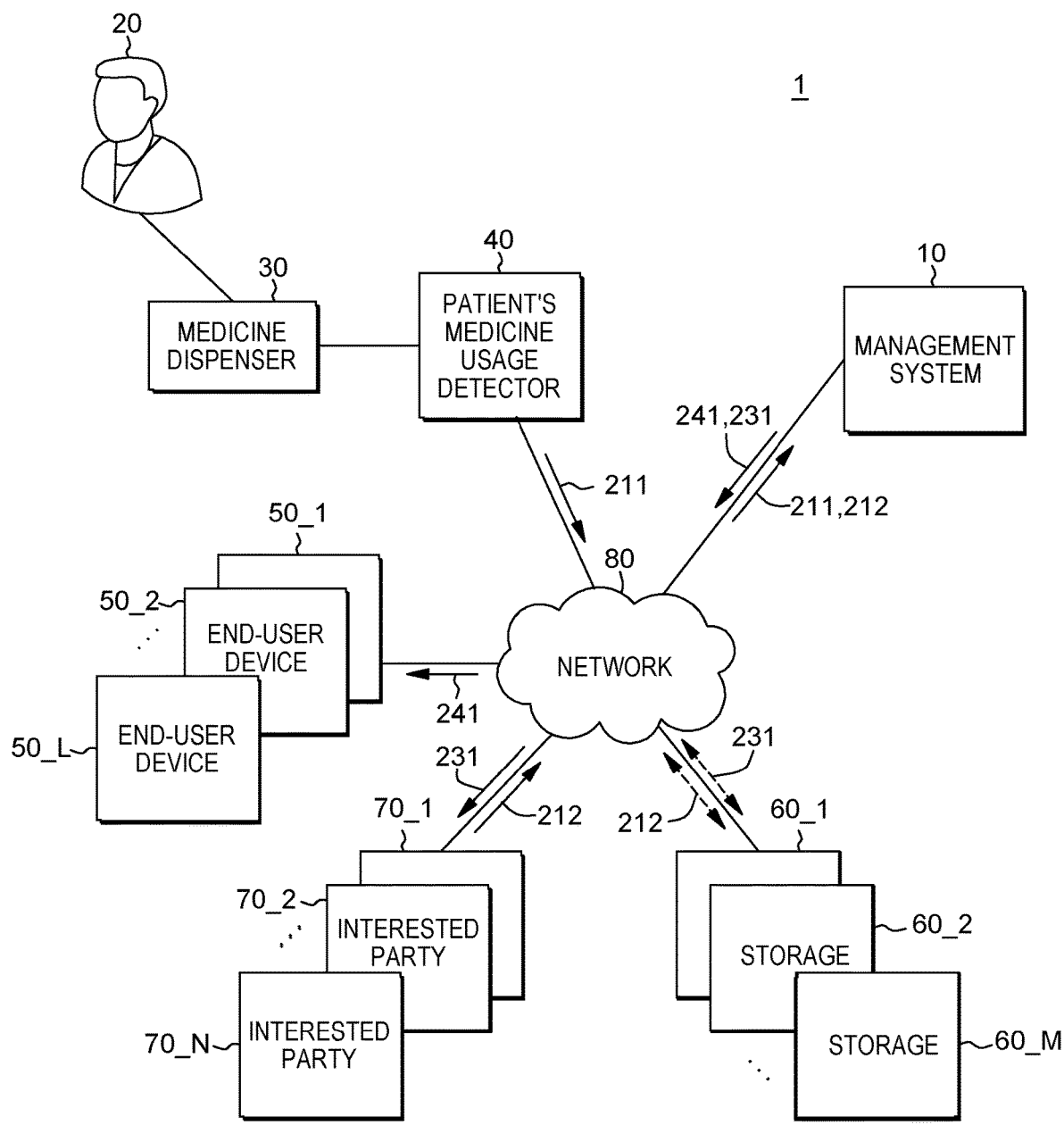
FIG. 1 depicts an example network environment for validating a medical adherence of a patient according to an exemplary embodiment of the present disclosure.

FIG. 1 depicts an example network environment 1 for validating a medical adherence of a patient according to an exemplary embodiment of the present disclosure.

Referring now to the example depicted in FIG. 1, the network environment 1 may include a management system 10, a medicine dispenser 30, a patient's medicine usage detector 40, one or more end-user devices 50_1 to 50_L, one or more storage systems, e.g., databases 60_1 to 60_M, one or more interested parties 70_1 to 70_N, and a network 80. Here, each of L, M, and N is an integer equal to or greater than one. The management system 10, the medicine dispenser 30, the patient's medicine usage detector 40, the one or more end-user devices 50_1 to 50_L, the one or more storage systems 60_1 to 60_M, and the one or more interested parties 70_1 to 70_N are interconnected via the network 80. For example, the network 80 may be configured to support communications among the management system 10, the medicine dispenser 30, the patient's medicine usage detector 40, the end-user devices 50_1 to 50_L, the storage systems 60_1 to 60_M, and the interested parties 70_1 to 70_N using wired communications based on Internet, local area network (LAN), wide area network (WAN), or the like, or wireless communications based on code division multiple access (CDMA), global system for mobile communication (GSM), wideband CDMA, CDMA-2000, time division multiple access (TDMA), long term evolution (LTE), wireless LAN, Bluetooth, near field communication (NFC), radio-frequency identification (RFID), or the like.

The management system 10 may refer to a cloud-based network system or platform configured to provide various services. The various services may include: collecting/processing various information or data (e.g., medicine usage data 211, etc.) collected from the patient's medicine usage detector 40; providing the processed information or data to other interested parties 70_1 to 70_N; or controlling operations of the one or more end-user devices 50_1 to 50_L within a specific environment of a patient 20, or other external environments of the remotely located family members or caregivers of the patient 20 based on the processed information or data. To this end, the management system 10 may include a framework of hardware, software, firmware, or any combination thereof (not shown).

Figure 2:
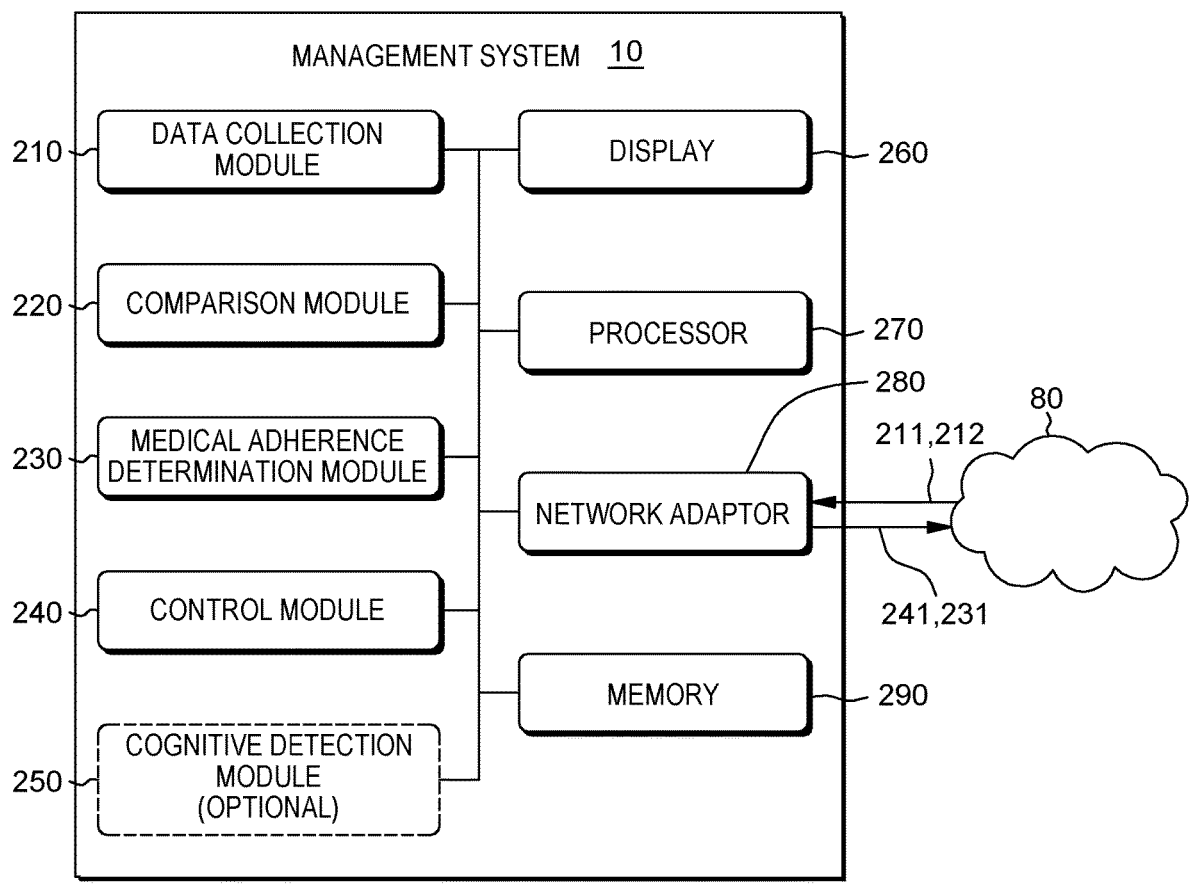
FIG. 2 is an example block diagram of a management system according to an exemplary embodiment of the present disclosure.

FIG. 2 is an example block diagram of the management system 10 according to an exemplary embodiment of the present disclosure.

As depicted in FIG. 2, the management system 10 includes a data collection module 210, a comparison module 220, a medical adherence determination module 230, and a control module 240. The management system 10 may further include a display device 260, a processor 270, a network adaptor 280, and a memory 290. Further, as described above, a cognitive detection module 250 for supporting a cognitive system may be included in the management system 10.

Referring to FIGS. 1 and 2, the data collection module 210 may be configured, designed, and/or programmed to collect or (or receive) medicine usage data 211. The medicine usage data 211 may be provided by the patient's medicine usage detector 40 using the network adaptor 280 via the network 80, as depicted in FIG. 2. The data collection module 210 may further receive prescription information including medicine prescription data 212, which is associated with the patient 20 provided by the one or more of healthcare providers (e.g., 70_1 of FIG. 1) such as physicians, pharmacists, etc. In one embodiment, the medicine prescription data 212 are stored and retrieved in/from the memory 290 or the one or more of the storage systems 60_1 to 60_M and retrieved.

The prescription data 212 may include, but are not limited to: a prescription ID, patient's personal information (e.g., healthcare member ID, name, address, social security number, etc.), usage instructions, etc. For example, the usage instructions include, but are not limited to: a type (or name) of medicine or combinations of medicines to be taken, the number or amount of medicine to be taken in a certain period (e.g., a day), an amount of medicines (e.g., the number of pills, the number of eye drops, the number of injections, etc.) to be taken each time, and a time interval between medicine usages.

The comparison module 220 may be configured, designed, and/or programmed to compare the medicine usage data 211 with the prescription data 212, and the medical adherence determination module 230 may be configured, designed, and/or programmed to determine whether the medicine is taken as prescribed in the prescription data 212 based on a comparison result of the medicine usage data 211 and the prescription data 212 provided by the comparison module 220.

The medical adherence determination module 230 may determine that the medicine is not taken as prescribed in response to detecting one or more mismatches between the medicine usage data 211 and the prescription data 212 in terms of one or more of various aspects such as: the number of doses, a time interval between medicine usages, a particular time at which the medicine is taken, etc.

In one example, in case where the prescription data 212 instructs to take a medicine three times a day and the medicine usage data 211 shows that the medicine is being taken less than three times (e.g., zero, once, or twice) a day, the medical adherence determination module 230 may determine that there exists a mismatch between the medicine usage data 211 and the prescription data 212, and provide a mismatch alert to the control module 240 (e.g., medical adherence is not determined). In some aspects, if the medicine usage data 211 is matched with the prescription data 222, the medical adherence determination module 230 may provide a match alert to the control module 240 (e.g., medical adherence is determined). In one embodiment, data of the medical adherence determined by the medical adherence determination module 230 may be stored in the memory 290 or in the one or more of the storage systems 60_1 to 60_M.

In another example, in case where the prescription data 212 instructs to take a medicine every, e.g., 8 hours, but the medicine usage data 211 shows that the medicine is being taken at different time interval (e.g., 6 hours or 10 hours) from the interval (e.g., 8 hours), the medical adherence determination module 230 may determine that there exists a mismatch between the medicine usage data 211 and the prescription data 212, and provide a mismatch alert to the control module 240 (e.g., medical adherence is not determined). In some aspects, if the medicine usage data 211 is matched with the prescription data 222, the medical adherence determination module 230 may provide a match alert to the control module 240 (e.g., medical adherence is determined).

The control module 240 may be configured, designed, and/or programmed to receive the mismatch alert or the match alert depending on whether the medicine usage data 211 is matched with the prescription data 212 or not. The control module 240 may generate one or more control signals 241 based on the mismatch or matched alert provided by the medical adherence determination module 230 and transfer the control signals 241 to one or more end-user devices 50_1 to 50_L within an environment (e.g., home or office) of the patient 20 or external environments of other persons (e.g., the family members of the patient 20, the caregivers of the patient 20, healthcare providers, etc.) using the network adapter 280 via the network 80, so that operations of the end-user devices 50_1 to 50_L can be controlled.

In one example, the end-user devices 50_1 to 50_L may include devices owned or used by the patient 20, the family members of the patient 20, or the caregivers of the patient 20, such as: a TV, a cell phone, an electronic game player, a smart watch, a vehicle, a home-automation system, a fitness tracker, an ultra-mobile PC (UMPC), a net-book, a personal digital assistant (PDA), a portable computer, a web tablet, a wireless phone, a mobile phone, a smart phone, a smart watch, an e-book, a portal media player (PMP), a portable game console, a digital camera, or the like, all of which may be connected to the management system 10 via the aforementioned network 80. In further examples, the control module 240 may extend control one or more end-user devices 50_1 to 50_L owned or used by the family members or caregivers of the patient 20 to enable the family members or caregivers to call or remind the patient 20 to take the medicine; in this example, the family members or caregivers may be located remotely from where the patient 20 is located.

In one embodiment, the control signals 241 may be used to control operations (e.g., disable or enable) of the end-user devices 50_1 to 50_L to remind the patient 20 that the medicine is not being taken as prescribed (e.g., non-medical adherence is determined) and encourage (or incentivize) the patient 20 to take the medicine as prescribed. For example, the management system 10 may use the control signals 241 to interface (or connect) one or more end-user devices 50_1 to 50_L within the environment of the patient 20, or the external environments of the remotely located family members or caregivers of the patient 20 to interrupt (or disable) or enable one or more operations of the end-user devices 50_1 to 50_L depending on whether the medicine is taken as prescribed.

In one embodiment, if a non-medical adherence (e.g., a mismatch alert between the medicine usage data 211 and the prescription data 212) is determined by the medical adherence determination module 230, the control module 240 may generate the control signals 241 to interrupt (or disable) the one or more operations of the end-user devices 50_1 to 50_L within the environment of the patient 20, or the external environments of the remotely located family members or caregivers of the patient 20 as a disincentive until the required medicine is taken as prescribed. For example, when interrupting (or disabling) operations of the end-user devices 50_1 to 50_L, the control module 240 may control the end-user devices 50_1 to 50_L to display a message (e.g., "patient needs to take a medicine"). Next, if a medical adherence (e.g., a match alert between the medicine usage data 211 and the prescription data 212) is determined by the medical adherence determination module 230, the control module 240 may generate the control signals 241 to release (or enable) the end-user devices 50_1 to 50_L from being interrupted as an incentive.

In one embodiment, the management system 10 may be configured to allow the patient 20, the family members of the patient 20, or the caregivers of the patient 20 to designate what end-user devices among the end-user devices 50_1 to 50_L can be used as incentives (or disincentives) to remind or prompt the patient 20 to take a medicine.

In one embodiment, one or more of the end-user devices 50_1 to 50_L may be internet of things (IOT)-enabled devices or may include at least one IOT-compliant hardware or software module, so that the management system 10 and the IOT-enabled end-user devices may be fully connected via the network 80. Also, one or more of the end-user devices 50_1 to 50_L may implement an application program interface (API) to allow the management system 10 to access and control the operations of the end-user devices 50_1 to 50_L.

Examples of the interrupting the operations of the end-user devices 50_1 to 50_L include, but are not limited to: displaying a message (e.g., "you need to take your medicine") on a TV or controlling a TV or a video player not to change channels; freezing or locking a game console; flashing a message on a cell phone; sending text messages or calling caregivers or family members automatically via a cell phone, etc. In other aspects, the management system 10 may interface wearable end-user devices such as a smart watch, etc., to control (or interrupt) the operations of other end-user devices.

In another embodiment, the management system 10 may interrupt specific applications of some end-user devices 50_1 to 50_L or websites accessible by the devices 50_1 to 50_L. To this end, for example, an agent may run on the end-user devices 50_1 to 50_L or firewall rules may be applied therein. For example, the management system 10 may block a cell phone from accessing specific websites related to, e.g., stocks, news, online shopping, social media, etc., and block a TV to show a favorite show of the patient 20, or favorite shows of the family members or caregivers of the patient 20 until the medicine is taken as prescribed.

As other examples, the patient 20 may need to take a medicine and wait for a prescription-instructed time (e.g., 2 hours) before he/she is allowed to drive his/her car (e.g., that medicine may be a pill for attention-deficit/hyperactivity disorder (ADHD) treatment that allows individuals to focus, but the medicine does not truly function for 2 hours after being taken). In this case, the management system 10 may initiate steps; to block a car (not shown) of the patient 20 from starting; or disable one or more operations of some end-user devices within environments of family members or caregivers of the patient 20 until it is determined that the prescription-instructed time elapses after the medicine being taken. Here, the car may include one of the end-user devices 50_1 to 50_L (e.g., IOT-enabled end-user devices) that allow the management system 10 to interface the car to prevent or enable a car engine ignition. In other aspects, the management system 10 may interface an end-user device (e.g., wearable end-user device) such as a smart watch, etc., to control the car's engine ignition or disable the operations of the end-user devices owned or used by the family members or caregivers of the patient 20.

In one aspect, the management system 10 may detect a medicine-taken time (e.g., a time at which a medicine is taken) using the patient's medicine usage detector 40, and if the prescription-instructed time (e.g., a time, e.g., 2 hours, for which the prescription instructs to wait before a specific action, e.g., drive a car) elapses after the medicine-taken time, the management system 10 may unlock a state of the car's engine ignition being prevented and allow the patient 20 to drive the car. In another aspect, at a certain time which the prescription-instructed time (e.g., 2 hours) elapses, the management system 10 may further ensure whether the medicine is functioning with a satisfied level before unlocking the state of the car's engine ignition being prevented or enabling the operations of the end-user devices of the family members or the caregivers of the patient 20. In one example, the management system 10 may receive a verification test result or a biological response with respect to, e.g., a cardiac cycle, a pulse, a blood pressure, etc. associated with the patient 20, using one or more user wearable devices and determine the medicine functioning if the verification test result or the biological response meets a predetermined criterion; in this example, the verification test result or the biological response may be generated by the wearable devices.

The above-mentioned features of the present application includes providing a cloud-based ecosystem that allows the end-user devices (e.g., IOT-enabled end-user devices) 50_1 to 50_L to be registered and governed for safety measures to protect patients (e.g., ADHD patient) against dangers if the patient does not take their medicines by blocking their cars from starting. As described above, their cars may be released from the blocked ignition state in response to determining that the medicine is taken as prescribed, the prescription-instructed time elapses after the medicine-taken time, and/or a corresponding verification test as to whether the medicine is functioning is passed.

In one embodiment, referring back to FIG. 2, the medical adherence determination module 230 may generate a medicine usage report 231 (e.g., metadata) recorded, e.g., over various time periods to the interested parties 70_1 to 70_N such as healthcare providers (e.g., physicians, pharmacist, etc.), healthcare companies, wellness rebate systems (e.g., "Cafewell" used at IBM), and/or the caregivers or family members of the patient 20. For example, the medicine usage report 231 may be transferred to computing systems of the interested parties 70_1 to 70_N or stored in the network storage systems 60_1 to 60_M to be retrieved by the computing systems of the interested parties 70_1 to 70_N when necessary; in another example, the medicine usage report 231 may be transferred to the family members or caregivers of the patient 20.

Figure 3:
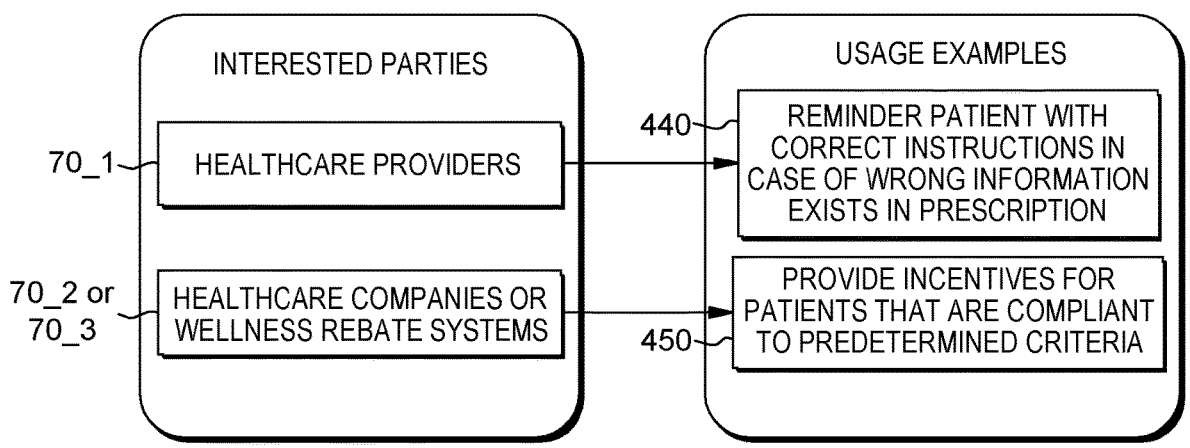
FIG. 3 is an example diagram illustrating how interested parties use a medicine usage report according to an exemplary embodiment of the present disclosure.

FIG. 3 is an example diagram illustrating how interested parties 70_1 to 70_N use a medicine usage report 231 according to an exemplary embodiment of the present disclosure.

As depicted in FIG. 3, if the healthcare providers 70_1 find lack of medicine usage or non-medical adherence (e.g., the medicine usage data 211 is not matched with the prescription data 212) based on the medicine usage report 231, they may determine that the patient 20 is no longer capable of taking the medicine for various reasons including a mental reason, a physical reason, or instructions in the prescription given from a physician or a pharmacist are confusing or incorrect (e.g., the physician writes a prescription to take a medicine once a day, but pharmacist erroneously indicates to take a medicine twice a day) and may remind the patient 20 with correct instructions, as described with reference to block 440.

The healthcare companies 70_2 may want the best value based outcome for their patients, which allow them to save money. It is one of the healthcare companies' best interests that they can verify that the patients are really taking the medicine correctly and encourage them to take the medicine if not taken as prescribed to prevent the patients from being hospitalized resulting in a more expensive claim. In addition, the wellness rebate systems 70_3 may use the medicine usage report 231 to assess whether to provide incentives (e.g., rebates, rewards, etc.).

Thus, the healthcare companies 70_2 or the wellness rebate systems 70_3 may provide the incentives for patients who are compliant to predetermined criteria (e.g., medical adherence is beyond a reference value), as described with reference to block 450.

Referring back to FIG. 1, the medicine dispenser 30 may include, but are not limited to: any shapes or kinds of containers or dispensers that dispense or store medicines such as a pill box, an eye drop bottle, an inhaled medicine, an injector, etc. Each dispenser 30 may be unique to a prescription ID/patient ID/pharmacy ID.

The patient's medicine usage detector 40 may refer to a system or platform configured to detect patient's behavior such as whether he/she is taking medicine as prescribed.

In one embodiment, at least a portion of the patient's medicine usage detector 40 may be implemented in or around the medicine dispenser 30. For example, one or more sensors may be disposed in or around the medicine dispenser 30 to sense whether the patient 20 is taking medicine as prescribed and send or store the sensed data to a memory (not shown) or radio-frequency identification (RFID) tag. The sensed data stored in the memory or the RFID tag will be transferred to the management system 10 via the network 80. In some embodiment, a mobile device (not shown) such as a cell phone, a smart watch, etc. can be used to receive and relay the sensed data to the management system 10 via the network 80.

In some embodiments, the one or more sensors disposed in or around the medicine dispenser 30 may include IoT sensors to enable remote sensing or monitoring of the medicine dispenser 30 with no or reduced human intervention (in real-time), and autonomous transmission of the sensor data to other systems interconnected thereto, such as the patient's medicine usage detector 40 or the management system 10.

In one embodiment, in case where the medicine dispenser 30 is a pill bottle, a sensor is configured to determine that a medicine is taken in response to detecting that a cap of the pill bottle is removed, the pill bottle is inverted, and/or a finger is inserted in the pill bottle. In some embodiment, the sensor may determine only when the above-detected actions on the pill bottle are detected in the above-described order.

In one embodiment, in case where the medicine dispenser 30 is an eye drop bottle, a sensor is configured to determine that a medicine is taken in response to detecting that a cap of the eye drop bottle is removed, the eye drop bottle is squeezed and inverted. In some embodiment, the sensor may determine only when the above-detected actions on the eye drop bottle are detected in the above-described order.

In one embodiment, in case where the medicine dispenser 30 is an inhaled medicine bottle, a sensor is configured to determine that a medicine is taken in response to detecting that the lip of the patient 20 is applied to the inhaled medicine bottle.

In one embodiment, implementations based on the sensor with wireless transmitter (e.g., RFID) can be replaced with a video camera (not shown) placed in or around a living environment of the patient 20. The video camera may be built in or attached to a mobile device, and/or may be implemented separately from the mobile device, but may communicate with the mobile device. By way of example, the video camera monitors the actions of the patient 20 to determine whether the patient 20 is taking a medicine as prescribed; the mobile device may: store one or more of prescription information (e.g., prescription ID) and personal information of the patient 20; analyze video images captured by the video camera as to whether the patient 20 is taking the medicine as prescribed; and report the analyzed data to the management system 10 via the network 80.

In one embodiment, a cognitive system can be used to analyze video images captured by the video camera to determine: whether the patient 20 is taking the medicine as prescribed; or medicine usage pattern of the patient 20. For example, the cognitive system may be implemented, using a machine-learning algorithm, in the management system 10 (e.g., the cognitive detection module 250) or in the mobile device.

In another scenario where the patient 20 uses a medicine (e.g., pill) reminder box (not shown) with daily grouping boxes as the medicine dispenser 30 to load/take medicines to/from the medicine reminder box. The patient 20, the family members of the patient 20, or the caregivers of the patient 20 may load medicines on each daily slot of the medicine reminder box and the patient's medicine usage detector 40 or the management system 10 may detect all the medicines loaded in all the daily slots of the medicine reminder box based on a medicine loading mode (e.g., load and sync). For example, the patient's medicine usage detector 40 or the management system 10 may record medicines being removed from bottles which are provided by a pharmacy and placed in an open slot in the medicine reminder box. This would work by placing a sensor on each daily slot of the medicine reminder box and allowing the sensor to detect loading of medicines when the slot is opened; for example, when each daily slot is opened, the patient's medicine usage detector 40 or the management system 10 may notice which slot is opened. When every slot is closed, each slot contains all required medicines taken out from each bottle (e.g., a lid of each slot is synchronized with all bottles that were opened). Thus, when a lid on a daily slot of the medicine reminder box is opened again, then the patient's medicine usage detector 40 or the management system 10 may determine all the medicines contained for that day corresponding to the daily slot are taken.

In one embodiment, one or more of the data collection module 210, the comparison module 220, the medical adherence determination module 230, the control module 240, the cognitive detection module 250 may be implemented using a hardware processor (e.g., 270 of FIG. 2) or based on a field-programmable-gate array (FPGA) design (not shown), but in other embodiments, they may be implemented based on program codes which are stored in a memory (e.g., 290 of FIG. 2) or in the hardware processor, and executed by the hardware processor.

Figure 4:
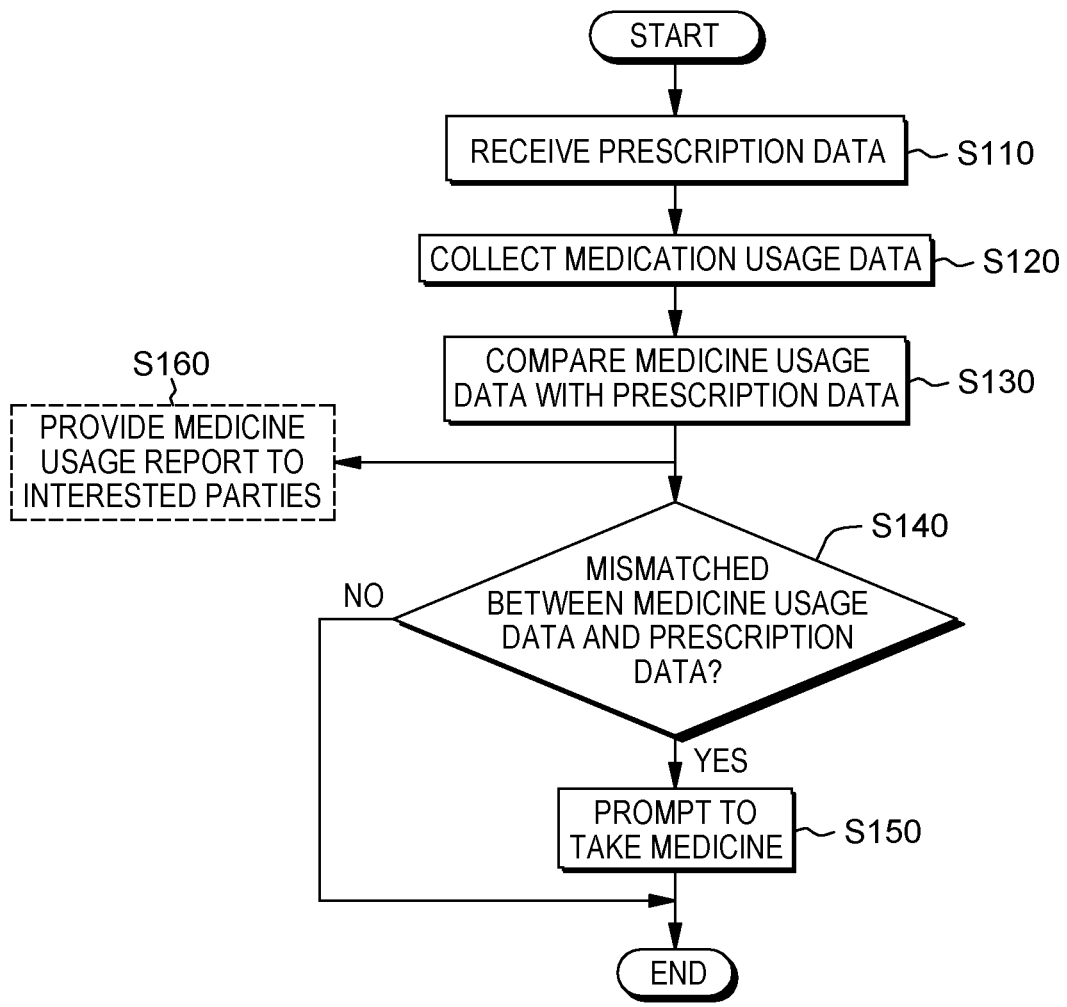
FIG. 4 is an example flow chart depicting a method for prompting a patient to take medicine as prescribed according to an exemplary embodiment of the present disclosure.

FIG. 4 is an example flow chart depicting a method for prompting a patient to take medicine as prescribed according to an exemplary embodiment of the present disclosure.

Referring to the example depicted in FIGS. 1, 2, and 4, the method may include steps S110 to S160.

At S110, the data collection module 210 may receive the prescription data 212 provided by the healthcare providers 70_1. Next, the data collection module 210 may also receive the medicine usage data 211 provided by the patient's medicine usage detector 40 (S120).

Next, at S130, the comparison module 220 may compare the medicine usage data 211 with the prescription data 212. If there exists a mismatch between the medicine usage data 211 and the prescription data 212 (YES) (S140) based on a comparing result provided as an outcome of the step S130, the control module 240 may take actions to prompt a patient (e.g., 20 of FIG. 1) to take a medicine (S150). If the medicine usage data 211 is matched with the prescription data 212 (NO) (S140), the method ends. The method may further include providing the medicine usage report 231 to one or more the interested parties 70_1 to 70_N at S160.

Figure 5:
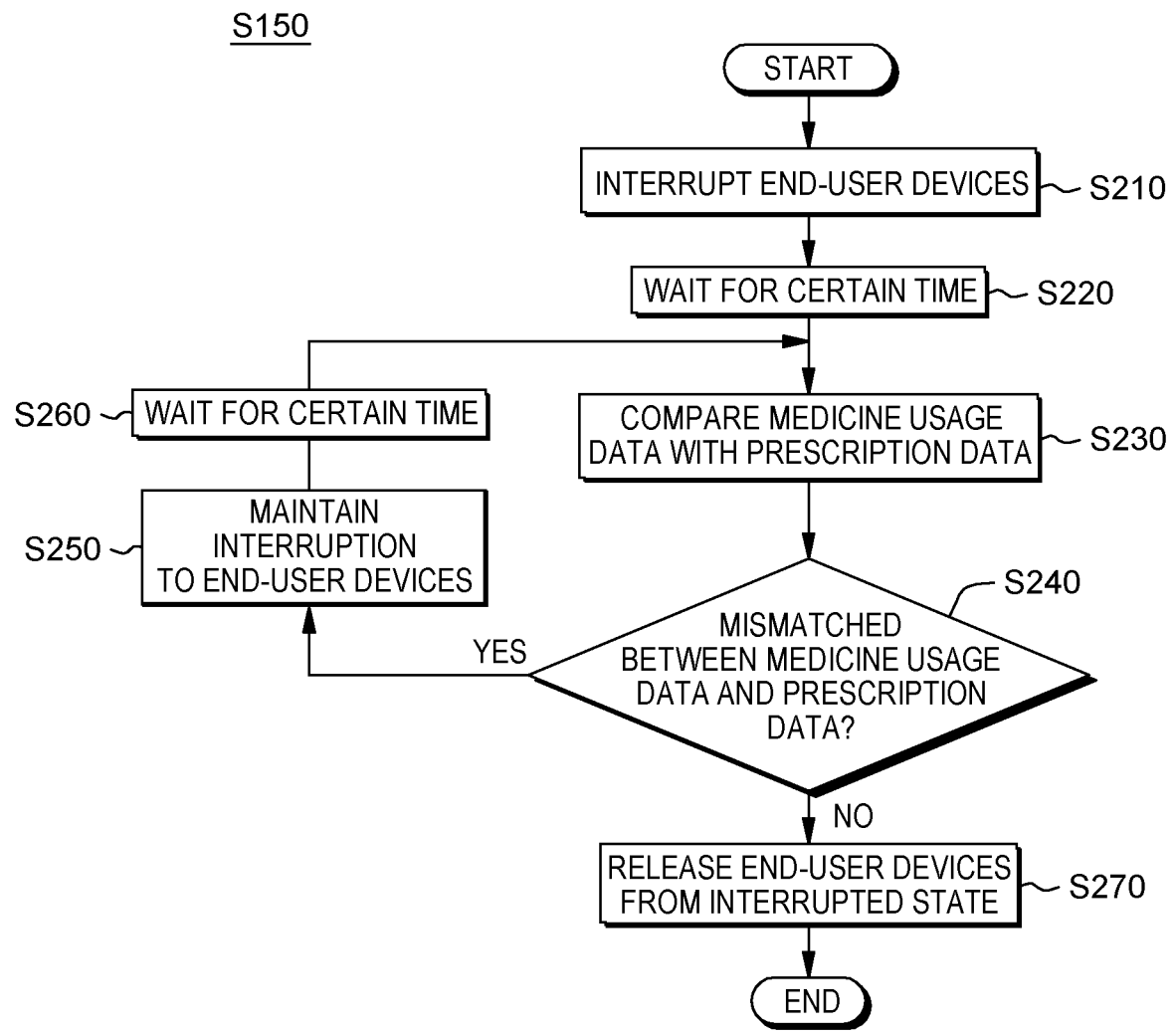
FIG. 5 is an example flow chart depicting details of step S150 of FIG. 4 according to an exemplary embodiment of the present disclosure.

FIG. 5 is an example flow chart depicting details of the step S150 of FIG. 4 according to an exemplary embodiment of the present disclosure.

Referring to the example depicted in FIGS. 1, 2, 4, and 5, the step S150 may include steps S210 to S270.

At S210, the control module 240 may generate and transfer the control signals 241 to one or more of the end-user devices 50_1 to 50_L within an environment of a patient (e.g., 20) or external environments of remotely located family members or caregivers of the patient to interrupt (or control) operations of the end-user devices 50_1 to 50_L until the medicine is taken as prescribed. Next, the comparison module 220 may compare the medicine usage data 211 with the prescription data 212 (S230) after waiting a certain time (S220). In addition, if there exists a mismatch between the medicine usage data 211 and the prescription data 212 (YES) (S240) based on a comparing result provided as an outcome of the step S230, the control module 240 may maintain the interruption to the end-user devices 50_1 to 50_L (S250) and repeat the steps S230 and S240 after waiting for a certain time (S260). If it is determined that the medicine usage data 211 is matched with the prescription data 212 (NO) in an operation of S240, the control module 240 may release the end-user devices 50_1 to 50_L from being interrupted (S270).

Figure 6:
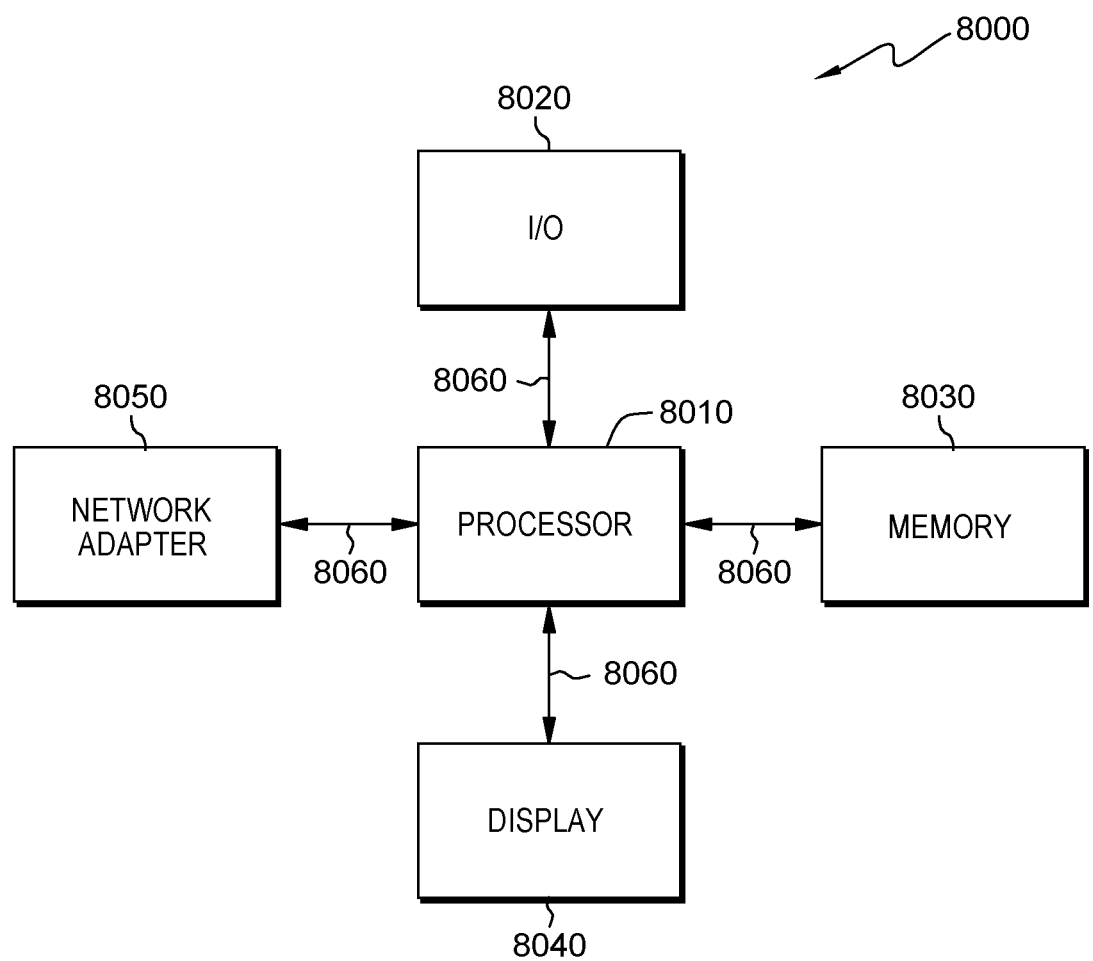
FIG. 6 is a block diagram of a computing system according to an exemplary embodiment of the present disclosure.

FIG. 6 is a block diagram of a computing system 8000 according to an exemplary embodiment of the present disclosure.

Referring to the example depicted in FIG. 6, a computing system 8000 may be used (without limitation) as a platform for performing (or controlling) the functions or operations described hereinabove with respect to the management system 10 of FIG. 1, and/or methods of FIGS. 4 and 5.

In addition (without limitation), the computing system 8000 may be implemented with a personal computer, a server, a workstation, a cloud-based computing system, an UMPC, a net-book, a PDA, a portable computer, a web tablet, a wireless phone, a mobile phone, a smart phone, an e-book, a PMP, or the like.

Referring now specifically to FIG. 6, the computing system 8000 may include a processor 8010, I/O devices 8020, a memory system 8030, a display device 8040, bus 8060, and a network adaptor 8050.

The processor 8010 is operably coupled to and may communicate with and/or drive the I/O devices 8020, memory system 8030, display device 8040, and network adaptor 8050 through the bus 8060.

The computing system 8000 can communicate with one or more external devices using network adapter 8050. The network adapter may support wired communications based on Internet, LAN, WAN, or the like, or wireless communications based on CDMA, GSM, wideband CDMA, CDMA-2000, TDMA, LTE, wireless LAN, Bluetooth, NFC, RFID, or the like.

The computing system 8000 may also include or access a variety of computing system readable media. Such media may be any available media that is accessible (locally or remotely) by a computing system (e.g., the computing system 8000), and it may include both volatile and non-volatile media, removable and non-removable media.

The memory system 8030 can include computer system readable media in the form of volatile memory, such as random access memory (RAM) and/or cache memory or others. The computing system 8000 may further include other removable/non-removable, volatile/non-volatile computer system storage media.

The memory system 8030 may include a program module (not shown) for performing (or controlling) the functions or operations described hereinabove with respect to the management system 10 of FIG. 1, and/or methods of FIGS. 4 and 5 according to exemplary embodiments. For example, the program module may include routines, programs, objects, components, logic, data structures, or the like, for performing particular tasks or implement particular abstract data types. The processor (e.g., 8010) of the computing system 8000 may execute instructions written in the program module to perform (or control) the functions or operations described hereinabove with respect to the management system 10 of FIG. 1, and/or methods of FIGS. 4 and 5. The program module may be programmed into the integrated circuits of the processor (e.g., 8010). In some embodiments, the program module may be distributed among memory system 8030 and one or more remote computer system memories (not shown).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++ or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present disclosure has been presented for purposes of illustration and description, but is not intended to be exhaustive or limited to the present disclosure in the form disclosed. Many modifications and variations will be apparent to those of ordinary skill in the art without departing from the scope and spirit of the present disclosure. The embodiment was chosen and described in order to best explain the principles of the present disclosure and the practical application, and to enable others of ordinary skill in the art to understand the present disclosure for various embodiments with various modifications as are suited to the particular use contemplated.

While the present disclosure has been particularly shown and described with respect to preferred embodiments thereof, it will be understood by those skilled in the art that the foregoing and other changes in forms and details may be made without departing from the spirit and scope of the present disclosure. It is therefore intended that the present disclosure not be limited to the exact forms and details described and illustrated, but fall within the scope of the appended claims.

What is claimed is:

1. A computer-implemented method for prompting a patient to take a medicine, comprising:
    collecting, at one or more processors, medicine prescription information associated with a patient;
    collecting, at the one or more processors, medicine usage data associated with the patient, said medicine usage data obtained from video images capturing a current medicine usage behavior of the patient;
    detecting, by the one or more processors, based on said captured current medicine usage behavior of the patient, a medicine usage pattern;
    determining, using a machine-learned model running at the one or more processors, that a medicine is taken by the patient as prescribed in the prescription information, the machine-learned model trained to detect a patient's compliance of medicine usage data with the prescription information based upon a matching of the detected medicine usage pattern associated with the captured medicine usage behavior of the patient and a prescribed medicine usage of the prescription information;
    generating a control signal and transmitting the control signal over a network connection for receipt at a network connected consumer electronics device within an environment of the patient or environments of the patient's family member or caregivers in response to determining that the medicine is not taken as prescribed; and
    disabling, responsive to receipt of the control signal, operation of the network connected consumer electronics device;
    generating, at the one or more processors, another control signal and transmitting the another control signal over the network connection for receipt at the network connected consumer electronics device in response to determining that the medicine is taken as prescribed, the determining that the medicine is taken as prescribed further comprising: receiving a further biological response directly from a biological sensor worn by said patient, and verifying the biological response meets a predetermined efficacy criterion; and
    releasing, responsive to receipt of the another control signal, the network connected consumer electronics device from being disabled.

2. The computer-implemented method of claim 1, further comprising:
    maintaining, at the one or more processors, the disabled operations of the consumer electronics device in response to determining that the medicine is not taken as prescribed.

3. The computer-implemented method of claim 1, wherein the collecting medicine usage data comprises capturing, using one or more sensors, one or more current patient behaviors comprising:
    opening or closing of a medicine dispenser;
    approaching of the patent's nose or mouth to the medicine dispenser;
    removing a cap of the medicine dispenser;
    squeezing of the medicine dispenser;
    inverting of the medicine dispenser; and
    inserting of the patent's finger in the medicine dispenser.

4. The computer-implemented method of claim 1, further comprising:
    providing a report about whether the medicine is taken by the patient as prescribed to at least one of healthcare providers, healthcare companies, the patient's family members, the patient's caregivers, and wellness rebate systems.

5. The computer-implemented method of claim 1, wherein the generating a control signal to interrupt operations of one or more devices comprises:
    selecting the consumer electronics device to be disabled based on an input provided by at least one of the patient, family members, and caregivers of the patient.

6. The computer-implemented method of claim 1, wherein the detecting a medicine usage pattern comprise one or more selected from: detecting a patient's actions of taking of one or more medicines or combinations of medicines at a defined time, taking of a number or amount of medicine in a certain time period or interval between medicine usages, or a taking of a certain number of pills, a certain number of eye drops, or a certain number of injections.

7. The computer-implemented method of claim 6, wherein the detecting a medicine usage pattern further comprises:
    determining that actions taken by the patient to dispense the medicine from a medicine dispenser are performed in a proper order.

8. A cognitive system for prompting a patient to take a medicine,
    one or more processors; and
    a memory, coupled to the one or more processors, the memory storing processor-executable program instructions,
    wherein the one or more processors, when executing the program instructions, are configured to:
    collect medicine prescription information associated with a patient;
    collect medicine usage data associated with the patient, said medicine usage data obtained from video images capturing a current medicine usage behavior of the patient;

detect, based on said captured current medicine usage behavior of the patient, a medicine usage pattern;

use a machine learned model to determine that a medicine is taken by the patient as prescribed in the prescription information, the machine-learned model trained to detect a patient's compliance of medicine usage data with the prescription information based upon a matching of the detected medicine usage pattern associated with the captured medicine usage behavior of the patient and a prescribed medicine usage of the prescription information;

generate a control signal and transmitting the control signal over a network connection for receipt at a network connected consumer electronics device within an environment of the patient or environments of the patient's family member or caregivers, in response to determining that the medicine is not taken as prescribed; and disable, responsive to receipt of the control signal, operation of the network connected consumer electronics device;

generate another control signal and transmitting the another control signal over the network connection for receipt at the network connected consumer electronics device in response to determining that the medicine is taken as prescribed, the determining that the medicine is taken as prescribed further comprising: receiving a further biological response directly from a biological sensor worn by said patient, and verifying the biological response meets a predetermined efficacy criterion, and release, responsive to receipt of the another control signal, the network connected consumer electronics device from being disabled.

9. The system of claim 8, wherein the one or more processors are further configured to:

maintain the disabled operations of the consumer electronics device in response to determining that the medicine is not taken as prescribed.

10. The system of claim 8, wherein to collect medicine usage data, the one or more processors are further configured to capture, using one or more sensors, one or more current patient behaviors comprising:

opening or closing of a medicine dispenser;
approaching of the patent's nose or mouth to the medicine dispenser;
removing a cap of the medicine dispenser;
squeezing of the medicine dispenser;
inverting of the medicine dispenser; and
inserting of the patent's finger in the medicine dispenser.

11. The system of claim 8, wherein the one or more processors are further configured to: provide a report about whether the medicine is taken by the patient as prescribed to at least one of healthcare providers, healthcare companies, the patient's family members, the patient's caregivers, and wellness rebate systems.

12. The system of claim 8, wherein to generate the control signal to disable the operations of the consumer electronics device, the one or more processors are further configured to: select the one or more devices to be disabled based on an input provided by at least one of the patient, family members, and caregivers of the patient.

13. The system of claim 8, wherein the one or more devices comprise an internet of things (IOT)-compliant hardware or software module.

14. The system of claim 8, wherein to detect a medicine usage pattern, the one or more processors are further configured to: detect a patient's actions of taking of one or more medicines or combinations of medicines at a defined time, taking of a number or amount of medicine in a certain time period or interval between medicine usages, or a taking of a certain number of pills, a certain number of eye drops, or a certain number of injections.

15. The system of claim 14, wherein to detect a medicine usage pattern, the one or more processors are further configured to:

determine that actions taken by the patient to dispense the medicine from a medicine dispenser are performed in a proper order.

16. A computer program product comprising a computer-readable storage medium having computer readable program instructions embodied therewith, the computer readable program instructions executable by at least one processor to cause a computer to perform a method for prompting a patient to take a medicine, comprising:

collecting medicine prescription information associated with a patient;

collecting medicine usage data associated with the patient, said medicine usage data obtained from video images capturing a current medicine usage behavior of the patient;

detecting, based on said captured current medicine usage behavior of the patient, a medicine usage pattern;

determining, using a machine learned model, that a medicine is taken by the patient as prescribed in the prescription information, the machine-learned model trained to detect a patient's compliance of medicine usage data with the prescription information based upon a matching of the detected medicine usage pattern associated with the captured medicine usage behavior of the patient and a prescribed medicine usage of the prescription information; and generating one or more control signals and transmitting the control signal over a network connection for receipt at a network connected consumer electronics device within an environment of the patient or environments of the patient's family member or caregivers, in response to determining that the medicine is not taken as prescribed; and disabling, responsive to receipt of the control signal, operation of the network connected consumer electronics device;

generating another control signal and transmitting the another control signal over the network connection for receipt at the network connected consumer electronics device in response to determining that the medicine is taken as prescribed, the determining that the medicine is taken as prescribed further comprising: receiving a further biological response directly from a biological sensor worn by said patient, and verifying the biological response meets a predetermined efficacy criterion, and releasing, responsive to receipt of the another control signal, the network connected consumer electronics device from being disabled.

17. The computer program product of claim 16, wherein the method further comprises:

maintaining the disabled operations of the consumer electronics device in response to determining that the medicine is not taken as prescribed.

18. The computer program product of claim 16, wherein the collecting capturing the patient's medicine usage behavior data comprises capturing, using one or more sensors, one or more current patient behaviors comprising:

opening or closing of a medicine dispenser;
approaching of the patent's nose or mouth to the medicine dispenser;
removing a cap of the medicine dispenser;
squeezing of the medicine dispenser;
inverting of the medicine dispenser; and
inserting of the patent's finger in the medicine dispenser.

19. The computer program product of claim 16, wherein the medicine usage pattern for detection comprises one or more selected from: detecting a patient's actions of taking of one or more medicines or combinations of medicines at a defined time, taking of a number or amount of medicine in a certain time period or interval between medicine usages, or a taking of a certain number of pills, a certain number of eye drops, or a certain number of injections.

20. The computer program product of claim 19, wherein the detecting a medicine usage pattern further comprises:
determining that actions taken by the patient to dispense the medicine from a medicine dispenser are performed in a proper order.

* * * * *